US008936106B2

(12) United States Patent  
Pedicini

(10) Patent No.: US 8,936,106 B2  
(45) Date of Patent: Jan. 20, 2015

(54) ELECTRIC MOTOR DRIVEN TOOL FOR ORTHOPEDIC IMPACTING

(71) Applicant: Christopher Pedicini, Nashville, TN (US)

(72) Inventor: Christopher Pedicini, Nashville, TN (US)

(73) Assignee: Medical Enterprises LLC, Nashville, TN (US)

( * ) Notice: Subject to any disclaimer, the term of this patent is extended or adjusted under 35 U.S.C. 154(b) by 0 days.

(21) Appl. No.: 14/332,790

(22) Filed: Jul. 16, 2014

(65) Prior Publication Data

US 2014/0318819 A1    Oct. 30, 2014

Related U.S. Application Data

(60) Continuation-in-part of application No. 12/980,329, filed on Dec. 29, 2010, now Pat. No. 8,695,726, and a division of application No. 13/790,870, filed on Mar. 8, 2013, now Pat. No. 8,602,124, which is a continuation of application No. 14/099,467, filed on Dec. 6, 2013, now abandoned, and a continuation-in-part of application No. 13/466,870, filed on May 8, 2012, now Pat. No. 8,393,409.

(51) Int. Cl.  
*B25D 17/00* (2006.01)  
*A61B 17/16* (2006.01)

(52) U.S. Cl.  
CPC ................................. *A61B 17/1626* (2013.01)  
USPC ............... 173/201; 173/2; 173/109; 173/132; 173/168

(58) Field of Classification Search  
USPC ............... 173/2, 48, 104, 109, 114, 132, 176, 173/181, 217  
See application file for complete search history.

(56) References Cited

U.S. PATENT DOCUMENTS

| 974,267 | A |  | 11/1910 | Hennessy |
|---|---|---|---|---|
| 4,143,585 | A |  | 3/1979 | Selsam |
| 5,057,112 | A | * | 10/1991 | Sherman et al. ................. 606/79 |
| 5,108,400 | A |  | 4/1992 | Appel et al. |
| 6,520,266 | B2 | * | 2/2003 | Bongers-Ambrosius et al. ................................. 173/2 |
| 6,644,418 | B2 | * | 11/2003 | Haga ............................... 173/48 |
| 6,938,705 | B2 |  | 9/2005 | Kikuchi |
| 7,001,393 | B2 |  | 2/2006 | Schwenke et al. |
| 7,318,485 | B2 | * | 1/2008 | Greese et al. ...................... 173/1 |
| 7,383,895 | B2 | * | 6/2008 | Aoki .............................. 173/201 |

(Continued)

FOREIGN PATENT DOCUMENTS

FR        EP 2 455 006         5/2012

*Primary Examiner* — Scott A. Smith  
(74) *Attorney, Agent, or Firm* — Aidenbaum Schloff and Bloom PLLC; Jay Schloff; Keith Schonberger

(57) ABSTRACT

An orthopedic impacting tool comprises a motor, an energy storage arrangement, a striker, and an anvil. The motor stores energy in the energy arrangement means and then releases it, causing the striker to apply a controlled force on an adapter to create a precise impact for use in a surgical setting. The tool may further comprise a combination anvil and adapter. The tool further allows forward or backward impacting for expanding the size or volume of the opening or for facilitating removal of a broach, implant, or other surgical implement from the opening. An energy adjustment control of the tool allows a surgeon to increase or decrease the impact energy. A light source and hand grips improve ease of operation of the tool.

20 Claims, 7 Drawing Sheets

(56) References Cited

U.S. PATENT DOCUMENTS

| | | | |
|---|---|---|---|
| 7,784,562 B2 * | 8/2010 | Ikuta | 173/201 |
| 7,861,799 B2 * | 1/2011 | Iwakami et al. | 173/201 |
| 7,926,584 B2 * | 4/2011 | John et al. | 173/1 |
| 8,069,929 B2 * | 12/2011 | Sugimoto et al. | 173/128 |
| 8,292,909 B1 | 10/2012 | DuBois et al. | |
| 8,393,409 B2 * | 3/2013 | Pedicini | 173/201 |
| 8,602,124 B2 * | 12/2013 | Pedicini | 173/201 |
| 8,695,726 B2 * | 4/2014 | Pedicini | 173/201 |

* cited by examiner

ELECTRIC MOTOR DRIVEN TOOL FOR ORTHOPEDIC IMPACTING

CROSS-REFERENCE TO RELATED APPLICATIONS

The present application is a continuation of and claims priority under 35 U.S.C. §120 on the U.S. patent application Ser. No. 14/099,467 (now abandoned), filed Dec. 6, 2013, the disclosure of which is incorporated by reference, which '467 application is a divisional application of U.S. patent application Ser. No. 13/790,870 (now U.S. Pat. No. 8,602,124), filed on Mar. 8, 2013, the disclosure of which is incorporated by reference, which '870 application was a continuation-in-part of and claimed priority under 35 U.S.C. §120 on U.S. patent application Ser. No. 12/980,329 (now U.S. Pat. No. 8,695,726), filed on Dec. 29, 2010, and U.S. patent application Ser. No. 13/466,870 (now U.S. Pat. No. 8,393,409), filed on May 8, 2012, the disclosures of which are incorporated by reference.

FIELD OF THE DISCLOSURE

The present disclosure relates to electric tools for impacting in orthopedic applications, and, more particularly, to an electric motor driven tool for orthopedic impacting that is capable of providing controlled impacts to a broach or other end effector.

BACKGROUND

In the field of orthopedics, prosthetic devices, such as artificial joints, are often implanted or seated in a patient's body by seating the prosthetic device in a cavity of a bone of the patient. Typically, the cavity must be created before the prosthesis is seated or implanted, and traditionally, a physician removes and or compacts bone to form this cavity. A prosthesis usually includes a stem or other protrusion that serves as the particular portion of the prosthesis that is inserted into the cavity.

To create such a cavity, a physician may use a broach, which broach conforms to the shape of the stem of the prosthesis. Solutions known in the art include providing a handle with the broach, which handle the physician may grasp while hammering the broach into the implant area. Unfortunately, this approach is clumsy and unpredictable as being subject to the skill of the particular physician. This approach almost will always inevitably result in inaccuracies in the location and configuration of the cavity. Additionally, the surgeon suffers from fatigue in this approach due to the constant hammering. Finally, this approach carries with it the risk that the physician will damage bone structure in unintended areas.

Another technique for creating the prosthetic cavity is to drive the broach pneumatically, that is, by compressed air. This approach is disadvantageous in that it prevents portability of an impacting tool, for instance, because of the presence of a tethering air line, air being exhausted from a tool into the sterile operating field and fatigue of the physician operating the tool. Further, this approach, as exemplified in U.S. Pat. No. 5,057,112, does not allow for precise control of the impact force or frequency and instead functions very much like a jackhammer when actuated. Again, this lack of any measure of precise control makes accurate broaching of the cavity more difficult.

A third technique relies on computer-controlled robotic arms for creating the cavity. While this approach overcomes the fatiguing and accuracy issues, it suffers from having a very high capital cost and additionally removes the tactile feedback that a surgeon can get from a manual approach.

A fourth technique relies on the author's own prior disclosures to use a linear compressor to compress air on a single stroke basis and then, after a sufficient pressure is created, to release the air through a valve and onto a striker. This then forces the striker to travel down a guide tube and impact an anvil, which holds the broach and or other surgical tool. This invention works quite well, but, in the process of testing it, does not allow for a simple method to reverse the broach should it become stuck in the soft tissue. Further, the pressure of the air results in large forces in the gear train and linear motion converter components, which large forces lead to premature wear on components.

Consequently, there exists a need for an impacting tool that overcomes the various disadvantages of the prior art.

SUMMARY OF THE INVENTION

In view of the foregoing disadvantages of the prior art, an electric motor-driven orthopedic impacting tool configured to include all the advantages of the prior art and to overcome the drawbacks inherent therein is provided. The tool may be used by orthopedic surgeons for orthopedic impacting in hips, knees, shoulders and the like. The tool is capable of holding a broach, chisel, or other end effector and gently tapping the broach, chisel or other end effector into the cavity with controlled percussive impacts, resulting in a better fit for the prosthesis or the implant. Further, the control afforded by such an electrically manipulated broach, chisel, or other end effector allows adjustment of the impact settings according to a particular bone type or other profile of a patient. The tool additionally enables proper seating or removal of the prosthesis or the implant into or out of an implant cavity and advantageously augments the existing surgeon's skill in guiding the instrument.

In an embodiment, an electric motor-driven orthopedic impacting tool comprises a power source (such as a battery), a motor, a control means, a housing, a method for converting the rotary motion of the motor to a linear motion (hereafter referred to as a linear motion converter), at least one reducing gear, a striker, a detent and an energy storage means, which energy storage means can include either compressed air or a vacuum. The tool may further include an LED, a handle portion with at least one handgrip for the comfortable gripping of the tool, an adapter configured to accept a surgical tool, a battery and at least one sensor. At least some of the various components are preferably contained within the housing. The tool is capable of applying cyclic impact forces on a broach, chisel, or other end effector, or an implant and of finely tuning an impact force to a plurality of levels.

In a further embodiment, the handle may be repositionable or foldable back to the tool to present an inline tool wherein the surgeon pushes or pulls on the tool co-linearly with the direction of the broach. This has the advantage of limiting the amount of torque the surgeon may put on the tool while it is in operation. In a further refinement of the hand grip, there may be an additional hand grip for guiding the surgical instrument and providing increased stability during the impacting operation.

In a further embodiment, the broach, chisel or other end effector can be rotated to a number of positions while still maintaining axial alignment. This facilitates the use of the broach for various anatomical presentations during surgery.

In a further embodiment the linear motion converter uses one of a slider crank, linkage mechanism, cam, screw, rack and pinion, friction drive or belt and pulley.

In an embodiment, the linear motion converter and rotary motor may be replaced by a linear motor, solenoid or voice coil motor.

In an embodiment, the tool further comprises a control means, which control means includes an energy adjustment element, and which energy adjustment element may control the impact force of the tool and reduce or avoid damage caused by uncontrolled impacts. The energy may be regulated electronically or mechanically. Furthermore, the energy adjustment element may be analog or have fixed settings. This control means allows for the precise control of the broach machining operation.

In an embodiment the anvil and the adapter comprise a single element, or one may be integral to the other.

In an embodiment the tool is further capable of regulating the frequency of the striker's impacting movement. By regulating the frequency of the striker, the tool may, for example, impart a greater total time-weighted percussive impact, while maintaining the same impact magnitude. This allows for the surgeon to control the cutting speed of the broach or chisel. For example, the surgeon may choose cutting at a faster rate (higher frequency impacting) during the bulk of the broach or chisel movement and then slow the cutting rate as the broach or chisel approaches a desired depth. In typical impactors, as shown in U.S. Pat. No. 6,938,705, as used in demolition work, varying the speed varies the impact force, making it impossible to maintain constant (defined as +/−20%) impact energy in variable speed operation.

In an embodiment the tool may have a lighting element to illuminate a work area and accurately position the broach, chisel, or other end effector on a desired location on the prosthesis or the implant.

In an embodiment the tool may also include a feedback system that warns the user when a bending or off-line orientation beyond a certain magnitude is detected at a broach, chisel, or other end effector or implant interface.

In an embodiment the tool may also include a detent that retains the striker and which may be activated by a mechanical or electrical means such that the energy per impact from the tool to the surgical end effector is increased. In an embodiment, the characteristics of this detent are such that within 30% of striker movement, the retention force exerted by the detent on the striker is reduced by 50%.

These together with other aspects of the present disclosure, along with the various features of novelty that characterize the present disclosure, are pointed out with particularity in the claims annexed hereto and form a part of the present disclosure. For a better understanding of the present disclosure, its operating advantages, and the specific objects attained by its uses, reference should be made to the accompanying drawings and detailed description in which there are illustrated and described exemplary embodiments of the present disclosure.

DESCRIPTION OF THE DRAWINGS

The advantages and features of the present invention will become better understood with reference to the following detailed description and claims taken in conjunction with the accompanying drawings, wherein like elements are identified with like symbols, and in which:

DETAILED DESCRIPTION OF THE DISCLOSURE

Figure 1:
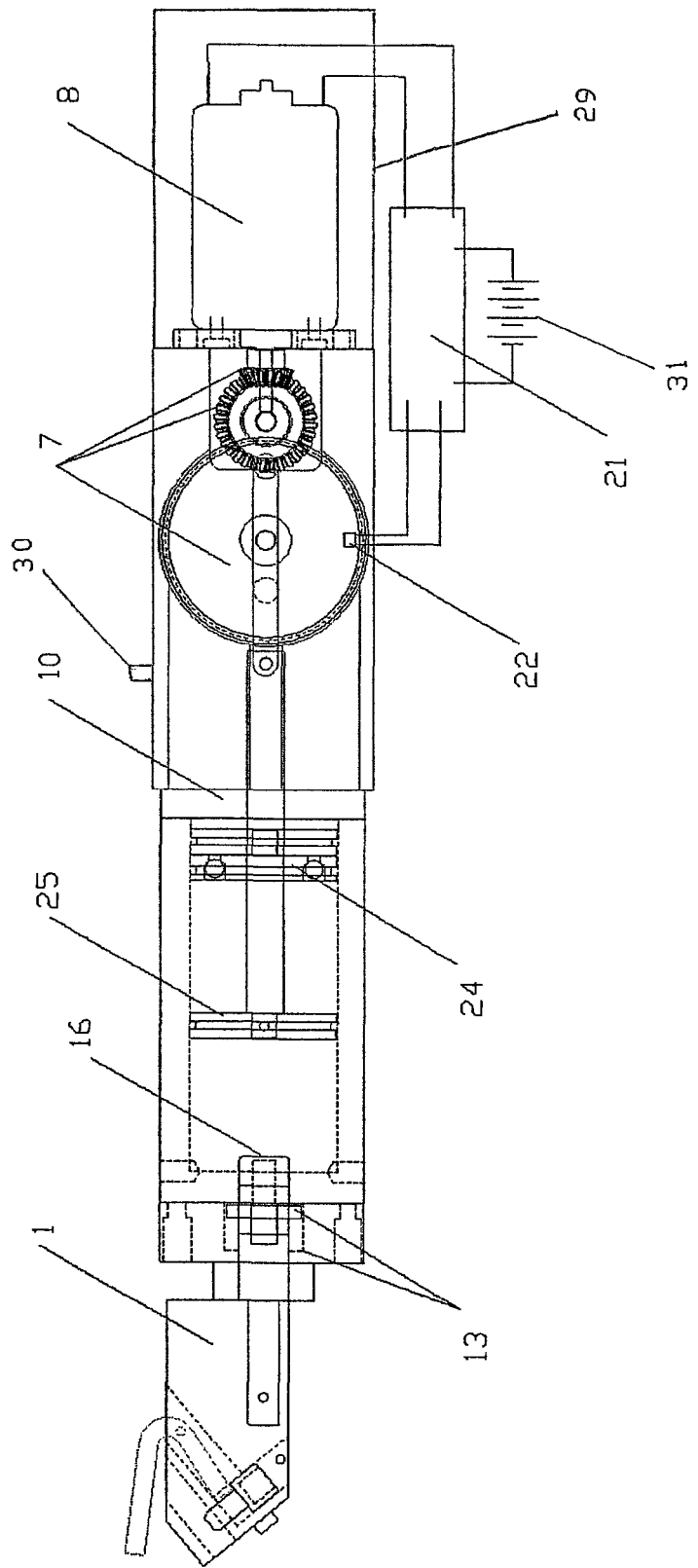
FIG. 1 shows a perspective view of an orthopedic impacting tool in accordance with an exemplary embodiment of the present disclosure in which a motor, linear motion converter, and vacuum as energy storage means are used.

The best mode for carrying out the present disclosure is presented in terms of its preferred embodiments, herein depicted in the accompanying figures. The preferred embodiments described herein detail for illustrative purposes are subject to many variations. It is understood that various omissions and substitutions of equivalents are contemplated as circumstances may suggest or render expedient, but are intended to cover the application or implementation without departing from the spirit or scope of the present disclosure.

The terms "a" and "an" herein do not denote a limitation of quantity, but rather denote the presence of at least one of the referenced items.

The present disclosure provides an electric motor-driven orthopedic impacting tool with controlled percussive impacts. The tool includes the capability to perform single and multiple impacts as well as impacting of variable and varying directions, forces and frequencies. In an embodiment the impact force is adjustable. In another embodiment a detent may be provided, which detent facilitates the generation of a higher energy impact. In yet another embodiment the impact is transferred to a broach, chisel, or other end effector connected to the tool.

The tool may further include a housing. The housing may securely cover and hold at least one component of the tool. In an embodiment, the housing contains a motor, at least one reducing gear, a linear motion converter, a gas chamber, a striker, a force adjuster, a control means, and an anvil.

The tool further may include a handle portion with at least one hand grip for comfortable and secure holding of the tool while in use, and an adapter, a battery, and a sensor, which sensor may be at least one of a positional sensor, a directional sensor, and a torsional sensor. The tool may further comprise a lighting element such as an LED to provide light in the work area in which a surgeon employs the tool. The anvil may be coupled to a broach, chisel or other end effector through the use of an adapter, which adapter may have a quick connect mechanism to facilitate rapid change of different broaching sizes. The anvil may further include a locking rotational feature to allow the broach to be presented to and configured at different anatomical configurations without changing the orientation of the tool in the surgeon's hands.

Referring now to FIGS. 1 through 4, in an embodiment, the linear motion converter 12 comprises a slider crank mechanism, which slider crank is operatively coupled to the motor 8 and reducing gears 7. The tool further comprises a vacuum chamber 23 that accepts a piston 24 which may be actuated by the linear motion converter 12. It will be apparent that the piston 24 may be actuated in more than one direction. The vacuum is created in the vacuum chamber 23 by the movement of piston 24 away from striker 25.

Figure 2:
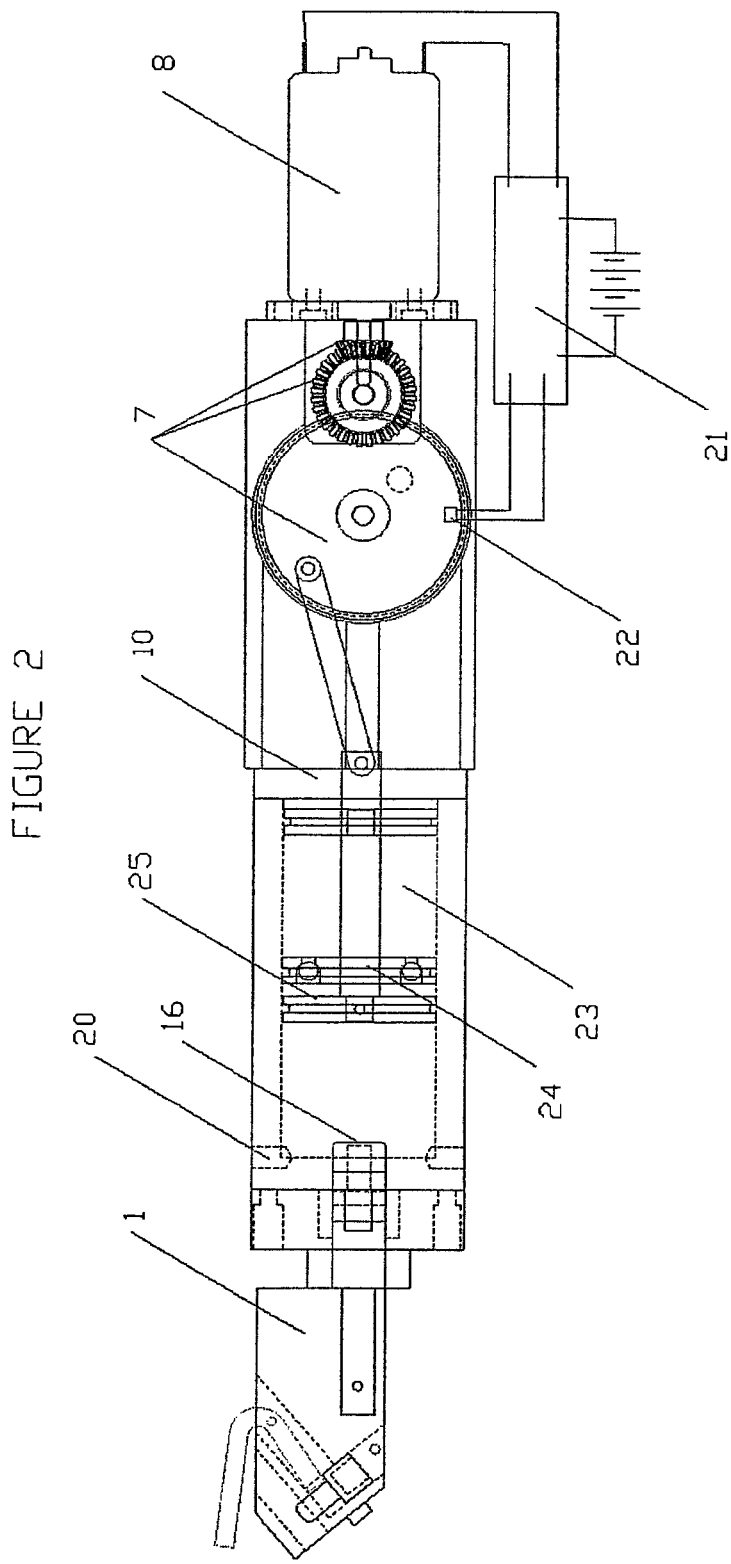
FIG. 2 shows an exemplary position of the piston wherein the vacuum has been created in accordance with an exemplary embodiment of the present disclosure.

In an embodiment, the motor 8 of the tool causes the linear motion converter 12 to move, which pulls a vacuum on the face of the striker 25 and creates at least a partial vacuum in the vacuum chamber 23, as is shown in FIG. 2. The piston 24 continues to move increasing the size of the vacuum chamber 23 until it hits a forward portion of the striker 25 (i.e., a portion of the strike that is proximate to the end effector or patient), which dislodges the striker 25 from its detent 10 and allows it to rapidly accelerate towards the end of the tool that is proximate to the end effector or patient. In an embodiment, the detent may be mechanical, electrical, or a combination thereof, with the preferred detent shown in the figures as a magnet. A characteristic of the detent 10 is that once the detent 10 is released or overcome, the retention force of the detent 10 on the striker 25 reduces by at least 50% within the first 30% movement of the striker 25. The impact of the striker 25 on the anvil 14 communicates a force to the adapter 1 and the broach, chisel or other orthopedic instrument.

In an embodiment, the direction of the force on the anvil is controlled by the user's (such as a surgeon) force on the tool and a stroke limiter 13. It has been determined that prior art tools may occasionally get stuck in a cavity and the impact of the striker in the aforementioned paragraph may be insufficient to dislodge the tool. This embodiment has the unexpected benefit of easily dislodging tools and instruments that have become stuck in a surgical cavity, while retaining all the benefits of the existing tool in terms of precision-controlled impacting. A user, such as a surgeon, may hold the tool by the hand grip 29 or grips and utilize the light emitted by an attached light source 30, such as an LED, to illuminate a work area of the tool. In an embodiment, the light source and/or other components of the tool may be powered by a power source, such as a battery 31.

In a further embodiment, an electromagnet may be incorporated as the detent 10 and released at an appropriate point in the operation cycle to allow the striker 25 to impact the anvil 14. Once the striker 25 has been released from the detent 10, the air pressure on the rearward side of the striker 25, propels it forward to impact the anvil 14 or other strike surface. The resultant force may be communicated through an end of the anvil 14 that is proximate to the anvil strike surface 16 and, optionally, through the adapter 1 to which a broach, chisel, or other end effector for seating or removing an implant or prosthesis may be attached.

The striker guide 11 may also have striker guide vent holes 20, which allow the air in front of the striker 25 to escape, thus increasing the impact force of the striker 25 on the anvil 14. The striker guide vent holes 20 may vent within the cavity of the tool body, thus creating a self-contained air cycle preventing air from escaping from the tool and allowing for better sealing of the tool. The position and the size of the striker guide vent holes 20 can also be used to regulate the impact force. Further, it was unexpectedly found that adding the striker guide vent holes 20 increases the impact force of the striker 25 on the anvil 14.

In an embodiment, as the piston 24 continues through its stroke it moves towards the rear direction, which movement brings it in contact with a rear face of striker 25 and moves it towards the rear of the tool. This allows the detent 10 to lock or retain the striker 25 in position for the next impact. The piston 24 completes its rearward stroke and preferably activates a sensor 22 that signals the motor 8 to stop such that the piston 24 rests at or near bottom dead center of the vacuum chamber 23. The vacuum chamber 23 preferably has a relief or check valve 9 or other small opening, which, in an embodiment, is part of the piston 24. The valve 9 may also be located at other points in the vacuum chamber 23 and allows for any air which may have accumulated in the vacuum chamber 23 to be purged out of the vacuum chamber 23 during each cycle. In a further embodiment this valve effect could be accomplished with a cup seal instead of an o-ring seal. This ensures that approximately atmospheric pressure is present in the vacuum chamber 23 at a starting point in the operational cycle, thus ensuring that each impact utilizes the same amount of energy, as is important in orthopedic impacting for at least the reason that it assures of a substantially consistent force and impact rate in multi-impact situations.

Figure 3:
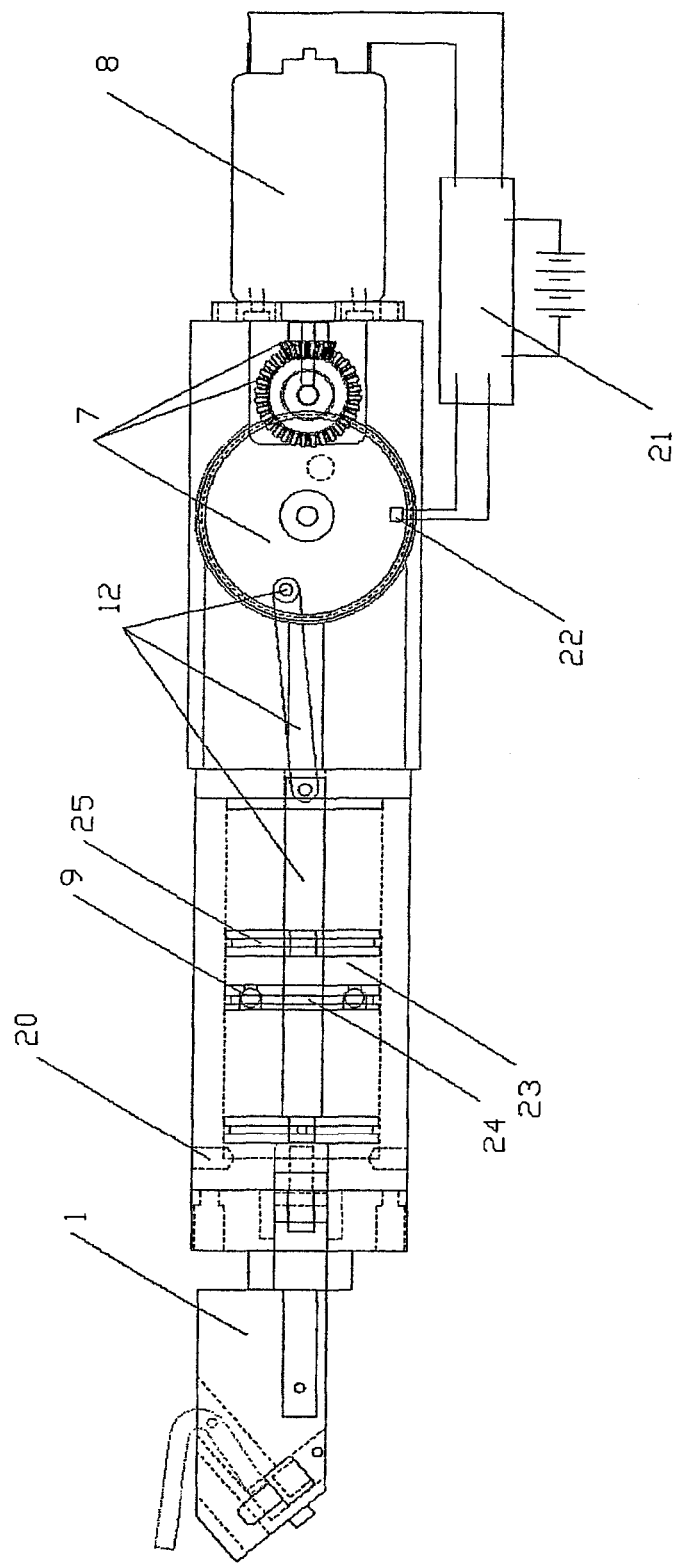
FIG. 3 shows the striker being released and the striker moving towards impacting the anvil in accordance with an exemplary embodiment of the present disclosure.
Figure 4:
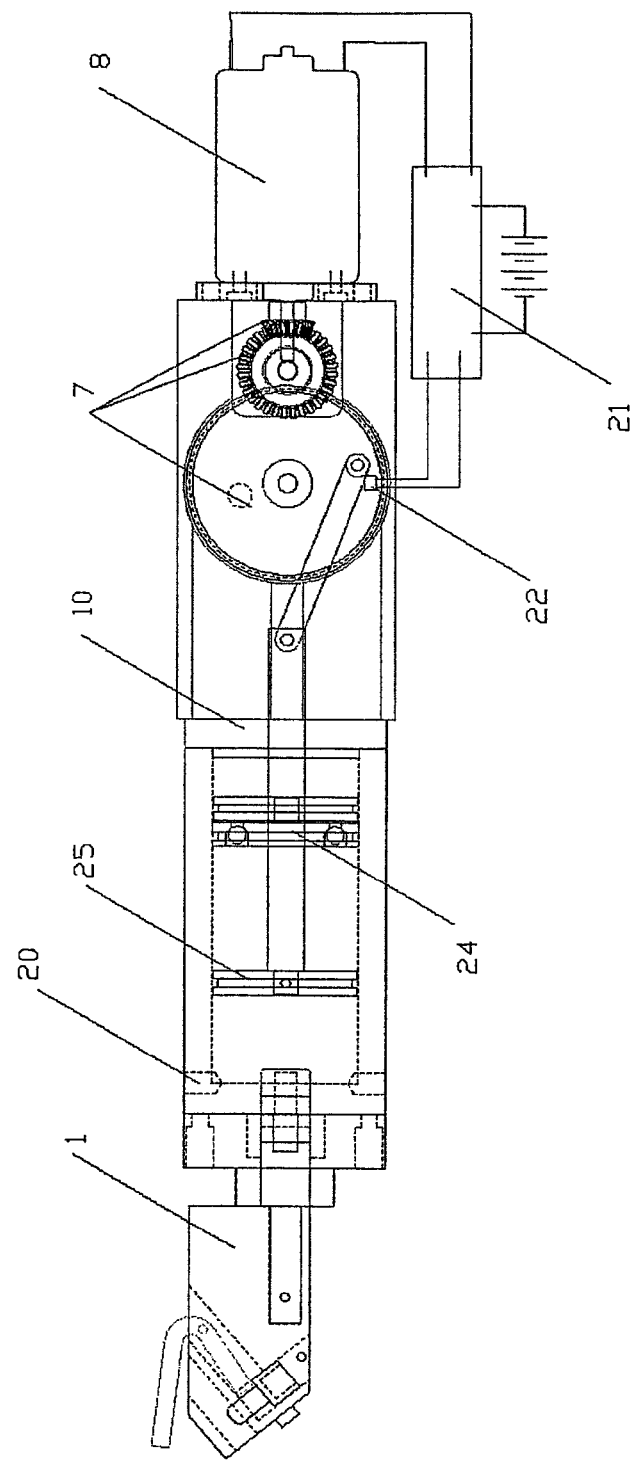
FIG. 4 shows the vacuum piston moving back towards a first position and resetting the striker in accordance with an exemplary embodiment of the present disclosure.

In a further embodiment, the motor 8 of the tool causes the linear motion converter 12 to move the piston 24 until the piston 24 moves a sufficient distance such that the forward portion of the piston impacts a portion of the striker 25 and overcomes the detent 10 that retains the striker 25 in the rear position. Once the striker 25 has been released from the detent 10, the vacuum in the vacuum chamber 23 exerts a force on the striker 25, which accelerates the striker 25, causing the striker 25 to slide axially down a cavity internal to the tool housing and strike the anvil strike surface 16. FIG. 3 shows the striker 25 imparting a force on the anvil strike surface 16, which causes a forward movement of the anvil 14 and/or tool holder. A resultant force may be communicated through an end of the anvil 14 that is proximate to the anvil strike surface 16 and, optionally, through the adapter 1 to which a broach, chisel, or other end effector for seating or removing an implant or prosthesis may be attached.

Figure 5:
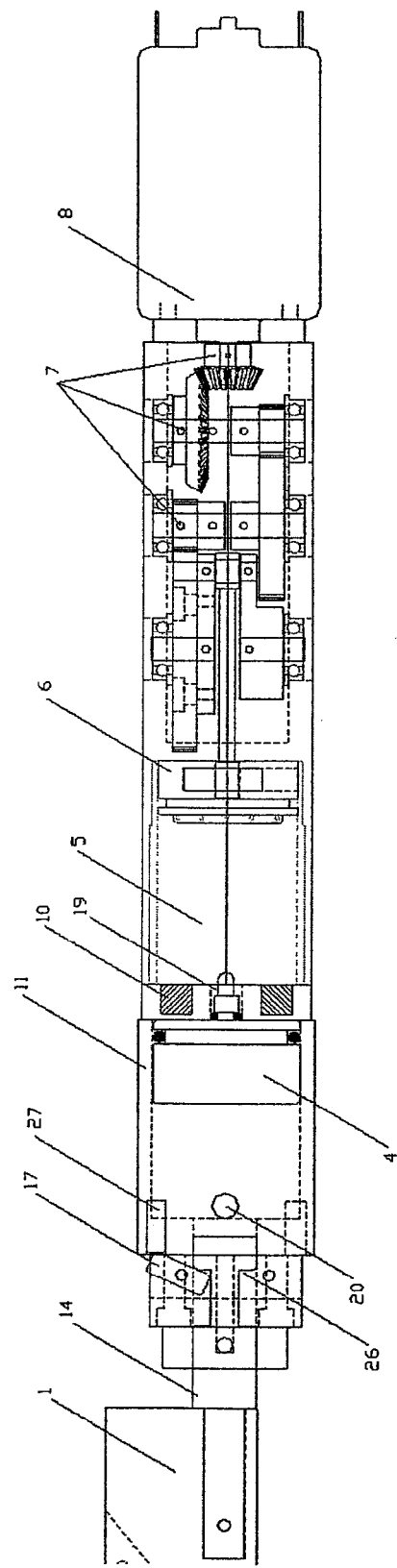
FIG. 5 shows an orthopedic impacting tool in accordance with an exemplary embodiment of the present disclosure in which a compression chamber is used to create an impacting force.
Figure 6:
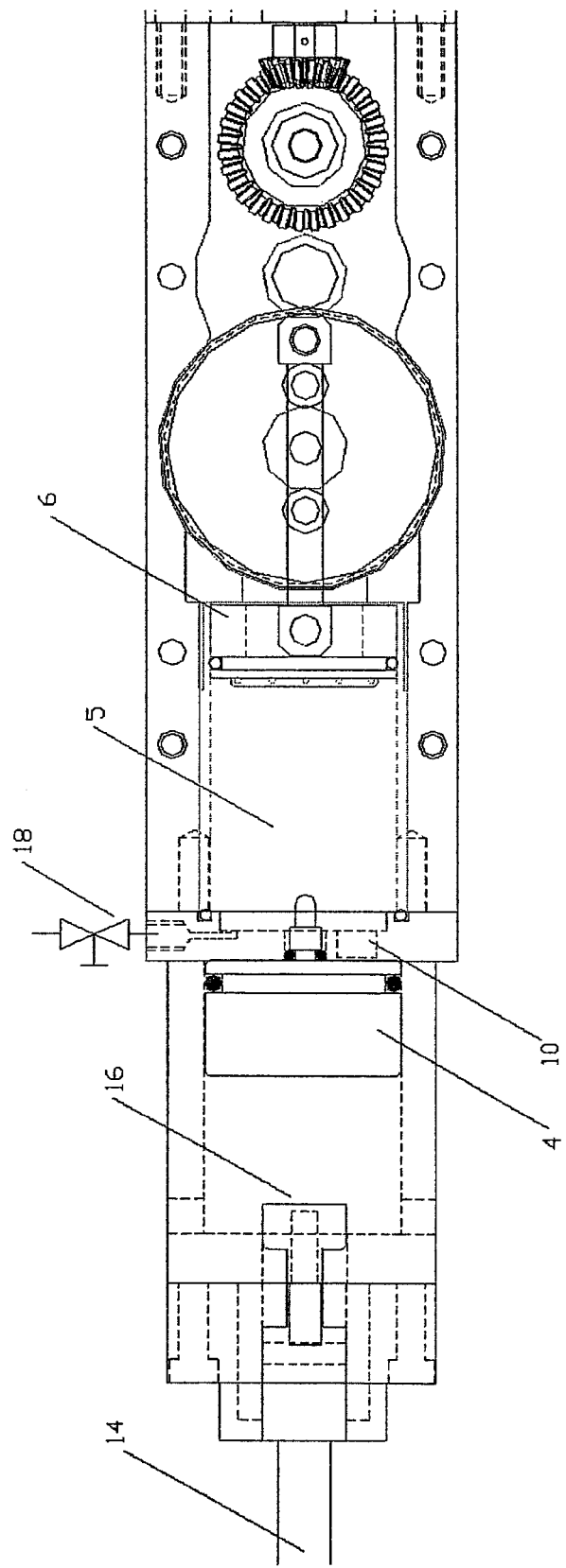
FIG. 6 shows an orthopedic impacting tool in accordance with an exemplary embodiment of the present disclosure in which a valve is used to adjust the energy of the impact of the striker.

In another embodiment, the impact force may be generated using a compressed air chamber 5 in conjunction with a piston 6 and striker 4, as shown in FIGS. 5 and 6. In this embodiment, the motor 8 of the tool causes the linear motion converter 12 to move the piston 6 until sufficient pressure is built within the compressed air chamber 5 that is disposed between the distal end of the piston 6 and the proximate end of the striker 4 to overcome a detent 10 that otherwise retains the striker 4 in a rearward position and or the inertia and frictional force that holds the striker 4 in that rearward position. Once this sufficient pressure is reached, an air passageway 19 is opened and the air pressure accelerates the striker 4, which striker 4 slides axially down a cavity and strikes the anvil 14. The air passageway 19 has a cross sectional area of preferably less than 50% of the cross sectional area of the striker 4 so as to reduce the amount of retaining force required from detent 10. The resultant force is communicated through the end of the anvil 14 that is proximate to the anvil strike surface 16 and, optionally, through the adapter 1 to which a broach, chisel, or other device for seating or removing an implant or prosthesis may be attached.

As the piston 6 continues through its stroke, it moves towards the rear direction, pulling a slight vacuum in compressed air chamber 5. This vacuum may be communicated through an air passageway 19 to the back side of the striker 4, creating a returning force on the striker 4, which returning force causes the striker 4 to move in a rear direction, i.e., a direction away from the point of impact of the striker 4 on the anvil strike surface 16. In the event that an adapter 1 is attached to the anvil 14, a force may be communicated through the adapter 1 to which the broach, chisel, or other end effector for seating or removing an implant or prosthesis is attached.

The tool may further facilitate controlled continuous impacting, which impacting is dependent on a position of a start switch (which start switch may be operatively coupled to the power source or motor, for example.) For such continuous impacting, after the start switch is activated, and depending on the position of the start switch, the tool may go through complete cycles at a rate proportional to the position of the start switch, for example. Thus, with either single impact or continuous impacting operational modes, the creation or shaping of the surgical area is easily controlled by the surgeon.

A sensor 22 coupled operatively to the control means 21 may be provided to assist in regulating a preferred cyclic operation of the linear motion converter 12. For example, the sensor 22 may communicate at least one position to the control means 21, allowing the linear motion converter 12 to stop at or near a position in which at least 75% of a full power stroke is available for the next cycle. This position is referred to as a rest position. This has been found to be advantageous over existing tools in that it allows the user to ensure that the tool impacts with the same amount of energy per cycle. Without this level of control, the repeatability of single cycle impacting is limited, reducing the confidence the surgeon has in the tool.

The tool is further capable of tuning the amount of impact energy per cycle by way of, for example, an energy control element 18. By controlling the impact energy the tool can avoid damage caused by uncontrolled impacts or impacts of excessive energy. For example, a surgeon may reduce the impact setting in the case of an elderly patent with osteoporosis, or may increase the impact setting for more resilient or intact athletic bone structures.

In an embodiment, the energy control element 18 preferably comprises a selectable release setting on the detent 10 that holds the striker 4 or 25. It will be apparent that the striker 4 or 25 will impact the anvil 14 with greater energy in the case where the pressure needed to dislodge the striker 4 or 25 from the detent 10 is increased. In another embodiment, the detent 10 may comprise an electrically controlled element. The electrically controlled element can be released at different points in the cycle, thus limiting the size of the vacuum chamber 23, which is acting on the striker 4 or 25. In an embodiment, the electrically controlled element is an electromagnet.

In another embodiment, the vacuum chamber 23 or compressed air chamber 5 may include an energy control element 18, which takes the form of an adjustable leak, such as an adjustable valve. The leakage reduces the amount of energy accelerating the striker 4 or 25, thus reducing the impact energy on the anvil 14. In the case of the adjustable leak, adjusting the leak to maximum may give the lowest impact energy from the striker 4 or 25, and adjusting to shut the leak off (zero leak) may give the highest impact energy from the striker 4 or 25.

Figure 7:
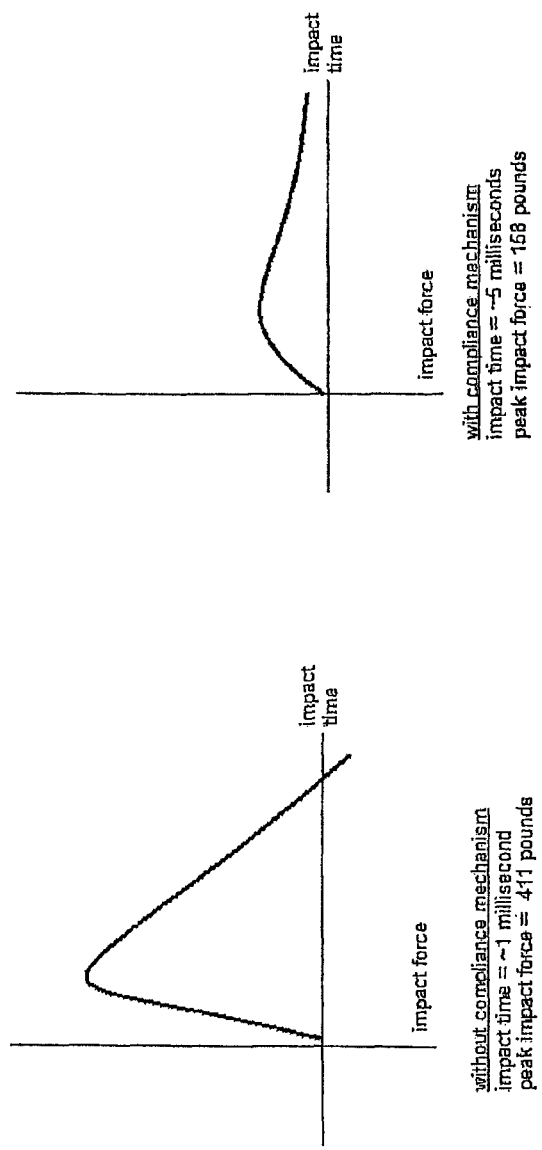
FIG. 7 shows a comparison of the force vs. time curve between a sharp impact and a modified impact using a compliance mechanism in accordance with an exemplary embodiment of the present disclosure.

The tool may further comprise a compliance means inserted between the striker 4 or 25 and the surgical end effector, which purpose is to spread the impact force out over a longer time period, thus achieving the same total energy per impact, but at a reduced force. This can be seen clearly as a result of two load cell tests on the instrument as shown in FIG. 7. This type of compliance means can limit the peak force during impact to preclude such peaks from causing fractures in the patient's bone. In a further embodiment, this compliance means may be adjustable and in a still further embodiment the compliance means may be inserted between striker 4 or 25 and the anvil 14 or surgical tool. In this manner and otherwise, the tool facilitates consistent axial broaching and implant seating. Preferably, the compliance means increases the time of impact from the striker to at least 4 milliseconds and preferable 10 milliseconds. This contrasts to impacting in which a very high force is generated due to the comparatively high strengths of the striker 4 or 25 and the anvil 14 (both steel, for example). Preferably, the compliance means comprises a resilient material such as urethane, rubber or other elastic material that recovers well from impact and imparts minimal damping on the total energy.

In a further embodiment, the adapter 1 may comprise a linkage arrangement or other adjustment means such that the position of the broach, chisel or other end effector can be modified without requiring the surgeon to rotate the tool. In an embodiment, the adapter 1 may receive a broach for anterior or posterior joint replacement through either an offset mechanism or by a rotational or pivotal coupling between the tool and the patient. The adapter 1 may thereby maintain the broach or surgical end effector in an orientation that is parallel or co-linear to the body of the tool and the striker 25. The adapter 1 may also comprise clamps, a vice, or any other fastener that may securely hold the broach, chisel, or other end effector during operation of the tool.

In use, a surgeon firmly holds the tool by the handle grip or grips and utilizes light emitted by the LED to illuminate a work area and accurately position a broach, chisel or other end effector that has been attached to the tool on a desired location on the prosthesis or implant. The reciprocating movement imparted by the tool upon the broach, chisel or other end effector allows for shaping a cavity and for seating or removal of a prosthesis.

The tool disclosed herein provides various advantages over the prior art. It facilitates controlled impacting at a surgical site, which minimizes unnecessary damage to a patient's body and which allows precise shaping of an implant or prosthesis seat. The tool also allows the surgeon to modulate the direction, force and frequency of impacts, which improves the surgeon's ability to manipulate the tool. The force and compliance control adjustments of the impact settings allow a surgeon to set the force of impact according to a particular bone type or other profile of a patient. The improved efficiency and reduced linear motion converter loads allow use of smaller batteries and lower cost components. The tool thereby enables proper seating or removal of the prosthesis or implant into or out of an implant cavity.

The foregoing descriptions of specific embodiments of the present disclosure have been presented for purposes of illustration and description. They are not intended to be exhaustive or to limit the present disclosure to the precise forms disclosed, and obviously many modifications and variations are possible in light of the above teaching. The exemplary embodiment was chosen and described in order to best explain the principles of the present disclosure and its practical application, to thereby enable others skilled in the art to best utilize the disclosure and various embodiments with various modifications as are suited to the particular use contemplated.

What is claimed is:

1. An orthopedic impacting tool for striking an object, the tool comprising:
   a motor;
   a linear motion converter;
   an energy storage means;
   a control means;
   at least one sensor, said at least one sensor operatively coupled to said control means;
   an adapter, said adapter capable of holding a broach, chisel, reamer, or other surgical implement; and
   a striker,
   wherein said control means directs said motor to store an energy in said energy storage means and said energy storage means thereafter releases the energy onto said striker causing said striker to move from a first position to a second position such that said striker is capable of imparting a force upon said adapter in at least one direction and said at least one sensor is used operatively with said control means to stop the tool in a rest position.

2. The tool as claimed in claim 1, wherein said energy storage means further comprises a valve.

3. The tool as claimed in claim 1, wherein said control means and said sensor allow for at least one of single percussive impacting and variable speed percussive impacting.

4. The tool as claimed in claim 1, wherein the tool further comprises an energy control element, said energy control element used to adjust the impact force of said striker.

5. The tool as claimed in claim 1, wherein the tool further comprises an air passageway, said air passageway used to communicate air from said energy storage means to said striker, said air passageway having a cross sectional area of less than fifty percent of a cross sectional area of said striker.

6. The tool as claimed in claim 1, wherein the tool further comprises a stroke limiter, said stroke limiter limiting a stroke of said adapter to less than fifty percent of a stroke of said striker.

7. The tool as claimed in claim 1, wherein said energy storage means comprises one of a compressed air chamber and a vacuum chamber.

8. The tool as claimed in claim 1, wherein the tool further comprises a detent, said detent retaining said striker in said first position until said detent is released or overcome thus allowing said energy storage means to release the energy onto said striker.

9. The tool as claimed in claim 8, wherein said detent comprises at least one of a magnet, electromagnet, solenoid, and mechanical interference.

10. An orthopedic impacting tool for striking an object, the tool comprising:
a linear motor;
an energy storage means;
a control means;
at least one sensor, said at least one sensor operatively coupled to said control means;
a surgical implement; and
a striker,
wherein said control means directs said motor to store an energy in said energy storage means and said energy storage means thereafter releases the energy onto said striker causing said striker to move from a first position to a second position such that said striker is capable of imparting a force upon said surgical implement in at least one direction and said at least one sensor is used operatively with said control means to stop the tool in a rest position.

11. The tool as claimed in claim 10, wherein said energy storage means further comprises a valve.

12. The tool as claimed in claim 10, wherein the tool further comprises an energy control element, said energy control element used to adjust the impact force of said striker.

13. The tool as claimed in claim 10, wherein the tool further comprises a stroke limiter, said stroke limiter limiting a stroke of said surgical implement to less than fifty percent of a stroke of said striker.

14. The tool as claimed in claim 10, wherein said energy storage means comprises one of a compressed air chamber and a vacuum chamber.

15. An orthopedic impacting tool for striking an object, the tool comprising:
a motor;
a linear motion converter;
an energy storage means;
a control means;
at least one sensor, said at least one sensor operatively coupled to said control means;
a surgical implement; and
a striker,
wherein said control means directs said motor to store an energy in said energy storage means and said energy storage means thereafter releases the energy onto said striker causing said striker to move from a first position to a second position such that said striker is capable of imparting a force upon said surgical implement in at least one direction and said at least one sensor is used to vary the frequency of the striker impacts.

16. The tool as claimed in claim 15, wherein said energy storage means further comprises a valve.

17. The tool as claimed in claim 15, wherein the tool further comprises an energy control element, said energy control element used to adjust the impact force of said striker.

18. The tool as claimed in claim 15, wherein the tool further comprises a stroke limiter, said stroke limiter limiting a stroke of said surgical implement to less than fifty percent of a stroke of said striker.

19. The tool as claimed in claim 15, wherein said energy storage means comprises one of a compressed air chamber and a vacuum chamber.

20. The tool as claimed in claim 15, wherein said linear motion converter comprises one of a slider crank, linkage mechanism, cam, screw, rack and pinion, friction drive, and belt and pulley.

* * * * *